United States Patent [19]

Hutton et al.

[11] Patent Number: 6,140,519

[45] Date of Patent: Oct. 31, 2000

[54] PROCESS FOR PRODUCING DEOILED PHOSPHATIDES

[75] Inventors: Kyle J. Hutton, Latham; John S. Guymon, Forsyth, both of Ill.

[73] Assignee: Archer-Daniels-Midland Company, Decatur, Ill.

[21] Appl. No.: 09/207,315

[22] Filed: Dec. 7, 1998

[51] Int. Cl.$^7$ ........................................... C07F 9/02
[52] U.S. Cl. ................ 554/83; 551/80; 551/82; 426/662
[58] Field of Search ................. 554/82, 83, 80; 426/662

[56] References Cited

U.S. PATENT DOCUMENTS

| | | | |
|---|---|---|---|
| 3,878,232 | 4/1975 | Hayes et al. | 260/412.4 |
| 4,062,882 | 12/1977 | Sen Gupta | 260/428.5 |
| 4,093,540 | 6/1978 | Sen Gupta | 210/23 F |
| 4,235,793 | 11/1980 | Betzing | 260/403 |
| 4,496,489 | 1/1985 | Sen Gupta | 260/428.5 |
| 4,533,501 | 8/1985 | Sen Gupta | 260/428 |
| 5,453,523 | 9/1995 | Weete et al. | 554/10 |
| 5,597,602 | 1/1997 | Peter et al. | 426/478 |
| 5,703,255 | 12/1997 | Weete et al. | 554/83 |

FOREIGN PATENT DOCUMENTS

| | | |
|---|---|---|
| 30 11 185 A1 | 10/1981 | Germany . |
| 275 461 A1 | 1/1990 | Germany . |
| 2-155989 | 6/1990 | Japan . |
| 1 509 543 | 5/1978 | United Kingdom . |

OTHER PUBLICATIONS

Dervwent Abstr., DD–275,461, Jan. 1990.
English translation of German Patent No. 275 461 A1.
Iwama, A., "New Process for Purifying Soybean Oil by Membrane Separation and an Economical Evaluation of the Process," in *Proceedings World Conference on Biotechnology for the Fats and Oils Industry*, T.H. Applewhite, ed., American Oil Chemist's Society, publ., pp. 244–250 (1988).
Koseoglu, S., et al., "Membrane Processing of Crude Vegetable Oils: Pilot Plant Scale Removal of Solvent from Oil Miscellas," *JAOCS* 67:315–322 (May 1990).
Schmidt, J., and Orthoefer, F.T., "Modified Lecithins," in *Lecithins*, B.F. Szuhaj and G.R. List eds., American Oil Chemist's Society, publ., pp. 203–211 (1985).
Dialog File 351: Derwent WPI, English Language Abstract of DE 30 11 185 A1, 1980.
Dialog File 351: Derwent WPI, English Language Abstract of DD 275 461 A1, 1990.
Dialog File 347: Japio, English Language Abstract of JP 63–308882, 1990.

*Primary Examiner*—Deborah D. Carr
*Attorney, Agent, or Firm*—Sterne, Kessler, Goldstein & Fox, P.L.L.C.

[57] ABSTRACT

The invention relates to a process for producing and refining phosphatides (phospholipids) including lecithin. Unlike previous procedures, the claimed process does not use acetone as a solvent, thereby yielding an acetone-free product suitable for animal or human consumption or for use as a pharmaceutical. The process produces phosphatides or lecithin with >90 A.I.

32 Claims, No Drawings

PROCESS FOR PRODUCING DEOILED PHOSPHATIDES

BACKGROUND OF THE INVENTION

1. Field of the Invention

The invention relates to deoiled phosphatides; food grade or pharmaceutical grade lecithin; and methods for producing same.

2. Related Art

The mixture of phosphatides referred to as lecithins is a mixture of naturally occurring fat soluble derivatives composed of the following structural members: glycerol, fatty acids, phosphoric acid, amino alcohols and carbohydrates. They are found in practically any animal and vegetable material. Commercial lecithin refers to this phospholipid mixture which is generally obtained by hydrating with water and removing the resultant gums formed by centrifugation from neutral triglyceride oil. One of the primary sources of lecithin is crude soybean oil.

Other oil bearing seeds such as corn germ and rapeseed yield lecithins, but are of lesser importance commercially. Lecithin produced by drying the gums contains 25–35% neutral triglycerides and 65–75% phosphatides, and is a plastic or viscous fluid product. This 65–75% phosphatides is referred to as 65–75% AI (acetone insolubles) due to the fact that in general the phosphatide fraction is insoluble in acetone. It is tested using AOCS (American Oil Chemists' Society) Method Ja 4–46.

In many applications, a solid granular or powdered product is desired. Such a product can be made by removing the neutral triglyceride oil from the lecithin. The art separates the oil by extracting with acetone ("*Lecithins*", B. Szuhaj and G. List, American Oil Chemists Society, 1985) and this is referred to as acetone deoiling. Until now, acetone deoiling has been the only commercially viable process for such preparation. Acetone deoiling suffers problems, however, in that as a solvent, acetone has a degree of toxicity. Additionally, residual amounts of acetone can remain in deoiled lecithin at levels of 5–10 ppm after desolventizing. Furthermore mesityl oxide, an acetone condensation product, can be present which imparts a significant off flavor. The acetone deoiled product must be analyzed routinely to carefully monitor both acetone and mesityl oxide residuals.

Because of the disadvantages associated with acetone extraction, alternative methods have been considered for processing of crude lecithin, such as using extraction with hydrocarbons (3–4 carbon atoms) under pressure (1–8 Mpa) with temperatures of from 20–100° C. (U.S. Pat. No. 5,597,602). Also the use of high pressure carbon dioxide has been suggested (DE-A 30 11 185).

Lipids may be separated from non-lipids and neutral lipids may be separated from polar lipids, especially phospholipids can be separated from neutral triglycerides using non-polar solvents and membrane separation. Non-polar solvents such as hexanes, chlorinated hydrocarbons, ethyl acetate may be separated from micelles with phospholipids which have molecular weights less than 50,000 daltons. These micelles act like macromolecules and are impermeable to ultra-filtration forming a retentate. They can thus be separated from the triglycerides which behave as single low molecular weight molecules in solution and pass through or permeate the membranes.

Phospholipids themselves may also be separated from one another in a similar manner using solubility and ultrafiltration techniques with more polar solvents such as alcohols.

Phospholipids have been separated from other components of crude vegetable oils. (U.S. Pat. No. 4,496,489, U.S. Pat. No. 4,062,882 and U.S. Pat. No. 4,533,501). For example, there are several methods that exist for refining crude soybean oil (British Patent No. 1,509,543, U.S. Pat. No. 3,878,232). There is also a process (British Patent No. 1,509,543) in which a crude hexane extract of the soybean, soybean oil miscella, is ultra-filtered under pressure through a suitable semipermeable membrane that allows the passage of a glyceride oil solution in hexane, but retains all the phospholipids together with sugars, sterol glucosides, etc., which form co-micelles with phospholipids in hexane solution. This process allows, a separation of phosphorous free lipids (e.g., triglycerides) from phospholipids and non-lipids (e.g., sugars) associated with them. The removal of hexane from the ultra-filtrate yields an oil free of phosphatides, whereas the retentate miscella yields commercial lecithin after hexane is removed.

None of the methods currently being used result in as pure or desirable a food grade lecithin as the process of the claimed invention because the known methods result in lower quality deoiled lecithin that can have an off flavor. Additionally, for currently produced lecithin including deoiled lecithin chemical bleaching agents much as hydrogen peroxide must be used to produce an acceptable light colored product. Therefore, the claimed process is easier to use for the commercial preparation of deoiled food grade lecithin.

SUMMARY OF THE INVENTION

The invention concerns the separation and refining of phosphatides, in particular soybean phosphatides to an oil-free state without the use of acetone as an extracting agent. It has been found that the claimed invention results in a higher quality lecithin that is made by a process that can be easily applied to commercial preparations.

The invention is first directed to a method for producing deoiled phosphatides, wherein the method does not use acetone and the retentate is decolorized following physical separation.

The invention is further directed to a method for producing deoiled phosphatides wherein the method comprises a further step of agglomeration.

The invention is further directed to a method of making phosphatides where a drum desolventizer is used. Preferably the drum desolventizer is chrome-plated iron or stainless steel.

The invention is further directed to methods of making phosphatides wherein there is a residual solvent concentration of less than 5 ppm.

The invention is further directed to a method for producing deoiled phosphatides, wherein the method does not use acetone, there is agglomeration of the phosphatide and the retentate may not be decolorized following physical separation.

A preferable embodiment for all the claimed methods is directed to the making of lecithin. A more preferred embodiment is drawn to methods of making lecithin that is >90 A.I.

The invention is further directed to a food grade or pharmaceutical grade lecithin, preferably characterized by >90 A.I.

DEFINITIONS

In order to provide a clear and consistent understanding of the specification and claims, including the scope to be given such terms, the following definitions are provided.

A. I. refers to "acetone insoluble matter" and is used as a measurement of purification. Crude lecithin is defined as having an A.I. of 40–90. A.I. can be determined by one of skill in the art by using AOCS (American Oil Chemists' Society Method Ja 4–46.

Bleaching Earth refers to various mined clays. These clays undergo commercial processing. Processing steps may include, but are not limited to such things as calcining, washing, drying, particle sizing and activation using various chemical treatments, as well as others performed by the commercial supplier. Bleaching earths may be readily obtained from commercial vendors (e.g. Süd Chemie, Germany) known to those of skill in the art. As an alternative to bleaching earths one could also use chemical means such as carbon, activated carbon, resins, chemical methods including but not limited to sodium hypochloride, peroxides and peracids.

Food and Pharmaceutical Grade Lecithin refers to lecithin having no residual acetone and that is >90 A.I.

Fractionated Lecithins refers to lecithins separated into subclasses or enriched fractions of lecithins. The subclasses or enriched fractions may be a mixture enriched in phospholipids comprising one or more but not limited to phosphatidyl choline, phosphatidyl ethanolamine, phosphatidyl serine, phosphatidyl inositol, phosphatidyl glycerol, diphosphatidyl glycerol, N-acylphosphatidyl ethanolamine, phosphatidic acid and plasmalogen.

Oil-free refers to lecithin with commercial residual oil specification of less than 3% oil. Deoiling is the process used to remove the oil from the starting material.

Lecithin generally refers to a complex, naturally occurring mixture of phosphatides obtained by water-washing crud vegetable oil and separating and drying the hydrated gums. They generally includes neutral triglyceride oil unless otherwise stated such as deoiled or granular, in which case the neutral oil has been removed. Soybean oil is the largest source of commercial lecithin. Other common oils yielding lecithins of lesser importance are corn, cottonseed, linseed, peanut, canola (rapeseed), safflower and sunflower. *Lecithins*, ed. Szhuhaj and List American Oil Chemists Society, 1985.

Modified Lecithin refers to but is not limited to acetylation, hydroxylation, hydrogenation, hydrolysis products of lecithin, chlorination, bromination, iodination, halogenation, phosphorylation and sulfonation. as well as any other modification known to those in the art as for example found in *Lecithins*, (eds. Szuhaj and G. List, pages 203–208, American Oil Chemists Society, 1985,) all of which is incorporated herein by reference. Lecithin contains a number of chemical functional groups that make it suscepible to a variety of chemical reactions. These groups include carbon-carbon double bonds, esters, phosphonate esters, amines and hydroxyl groups. Modification may also result in interesterified lecithin. Additionally, lecithins may be enzyme modified.

Permeate refers to material that passes through a membrane filter.

Phosphatides (Phospholipids) refers to but are not limited to mixtures of phosphatidyl choline, phosphatidyl ethanolamine, phosphatidyl serine, phosphatidyl inositol, phosphatidic acid, N-acylphosphatidyl ethanolamine and other related minor constituents.

Retentate refers to material that does not pass through a membrane filter.

DETAILED DESCRIPTION OF THE INVENTION

The present invention relates to deoiled phosphatides; food grade or pharmaceutical grade lecithin; and methods for producing same.

In one embodiment, the present invention relates to a method for producing deoiled phosphatides, the method not using acetone as a solvent and comprising:

a) mixing a crude phosphatide preparation with an alkane;

b) separating triglycerides from phosphatides through a membrane;

c) obtaining a retentate following separation;

d) decolorizing the retentate with bleaching earth;

e) evaporating the alkane from the retentate.

Preferably, the above-described method further comprises the step of granulating in a powder agglomerator.

In another embodiment, the present invention relates to a method for producing deoiled phosphatides, the method not using acetone as a solvent and comprising:

a) mixing a crude phosphatide preparation with an alkane;

b) separating triglycerides from phosphatides through a membrane;

c) obtaining a retentate following separation;

d) evaporating the alkane from the retentate; and e) granulating in a powder agglomeration.

In a further embodiment, the present invention relates to a method for producing food grade or pharmaceutical grade deoiled lecithin, the method not using acetone as a solvent and comprising:

a) mixing crude lecithin with an alkane;

b) separating triglycerides from phosphatides through a membrane;

c) obtaining a retentate following separation;

d) decolorizing the retentate with bleaching earth; and e) evaporating the alkane from the retentate.

Preferably, the above-described method further comprises the step of granulating in a powder agglomerator.

In another embodiment, the step involving decoloring with bleaching earth is replaced (either before evaporating or at an appropriate point in the method) with alternative decolorizing agents such as carbon, activated carbon, resins or chemical means included but not limited to use of peroxided sodium hypochorite or peracids.

In another embodiment, the present invention relates to a method for producing a food grade or pharmaceutical grade of deoiled lecithin, the method not using acetone as a solvent and comprising:

a) mixing crude lecithin with an alkane;

b) separating triglycerides from phosphatides through a membrane;

c) obtaining a retentate following separation;

d) evaporating the alkane from the retentate; and e) granulating in a powder agglomeration.

Preferably, the phosphatide or lecithin obtained by the above-described methods is virtually oil free and is >90 acetone insoluble matter (A.I.) (more preferably, >97 A.I., >99 A.I. or >99.9 A.I.).

Preferably, the above-described methods have a residual solvent concentration of less than 5 ppm (more preferably, less than 1 ppm, or less than 0.1 ppm).

Preferably the above described methods use a drum desolventizer to remove the alkane. More preferably the drum desolventizer is chrome-plated cast iron or stainless steel.

Preferably, the crude phosphatide used in the above-described methods is from a vegetable selected from the group consisting of soybean, corn, cotton-seed, linseed, peanut, canola, rapeseed, safflower and sunflower.

Preferably, the crude lecithin used in the above-described methods is from a vegetable selected from the group consisting of soybean, corn, cotton-seed, linseed, peanut, canola, rapeseed, safflower and sunflower.

Preferably, the mixed tocopherols used in the above-described methods are added after bleaching and before evaporating the alkane from the retentate.

Membrane separation technology is increasingly used in the refining of edible oils. Such technology allows for the physical separation of phosphatides or lecithin from other products in the crude starting material. The application of this technology and the membranes used in this technology are known to one of skill in the art and have been described in several publications. For example, see Japanese Application No. Showa 63–308882, Dec. 8, 1988, laid open Jun. 15, 1990: Kosseoglu, et al., *JAQCS* 67:315–322 (1990): Iwama, Proceedings of World Conf. Biotechnol. Fats and Oils Ind. 88.00,00 244–50 (1988). The choice of the specific membrane to use will obviously depend upon the solvent system being used to separate the components of interest. The main criteria for selection of the membrane is that it is resistant to the solvent being used and also allows the unwanted materials to pass through, thereby leaving the desired phospholipids on the retentate side.

The employment of a membrane (preferably, resistant to the solvent being used) is the principle means of physically separating the triglyceride from the phosphatides in a solvent based system where crude lecithin comprising a range of 40–90 A.I. phosphatides is mixed with commercial solvent (preferably, in a 1:1 mass ratio).

Many membrane types can be used effectively over a wide range of molecular weight cutoff. These include polysufones, polyamide, cellulose, polypropylene, polyvinylidine fluoride (PVDF), membranes on aluminum and other commercially available filters.

Preferably, the membrane has a molecular weight cutoff of 50,000 daltons or less. More preferably the membrane has a molecular weight cutoff of 10,000 daltons.

Also preferably, the membrane is compatible with the solvents described herein.

Further preferably, the membrane used in the above-described methods is a polyvinylidine fluoride (PVDF) membrane.

Preferably, the alkane used in the above-described methods is an alkane with 3–8 carbons. More preferably, the alkane used in the above-described methods is selected from the group consisting of hexane, heptane, pentane, propane, isooctane, butane, isohexane and cyclohexane. Alternatively supercritical $CO_2$ alone or with modifiers (e.g. other solvents) may be used as well.

The separation yields a permeate consisting of triglycerides and hexanes. The solvent is evaporated and the resulting oil is of higher quality when compared to the oil recovered in the acetone extraction process. This is due to lack of an off odor or of the mesityl oxide noted above. In addition commercial hexane is used in the extraction of crude oil from oil bearing seeds and seed byproducts. Thus by using hexane for both processes (i.e. preparation of the oil-free phosphatide and the oil permeate,) the additional separate solvent system for acetone is not needed resulting in a cost savings. The retentate consists of virtually oil free (>90 A.I.) phosphatides including an enhanced fraction of phosphatidyl choline when compared to the acetone derived product. The retentate can be 35–40% phospholipid in 60–65% hexane.

Because color bodies which are commercially objectionable remain with the phospholipid fraction during preparation of the phosphatides, a decolorization step is used.

This optional step also removes other impurities which can lead to premature oxidation. This step comprises the use of bleaching earth. Chlorophylls and xanthophylls and other prooxidants are absorbed, bleached or removed in this process. The earth is added to a vessel containing a 35–40% deoiled concentrate in hexane. A typical rate of addition is 5–8% earth on a phospholipid mass basis. The color bodies physically adsorb to the clay. The clay is then separated from the deoiled concentrate via dead end filtration.

If antioxidants are added to provide increased stability for the deoiled product, this point in the processing is a convenient opportunity to add them while the phosphatides are still in solution prior to evaporation of the solvent. Accordingly, antioxidants are preferably added before evaporating the hexane from the solvent. Preferred antioxidants are mixed tocopherols, however, others would be known to those of skill in the art.

Desolventizing removes the hexanes from the purified oil-free phospholipids. Many different means can be used to desolventize the product. These include but are not limited to spray dryers, fluid bed driers with or without vibration, drum driers, belt driers, tumble driers, all of these can be either batch or continuous.

Of key importance to the process is the use of drum desolventizers. The desolventizing drums can be chrome-plated cast iron or stainless steel. Low pressure steam is added as the heat source. The refined deoiled concentrate is added to the nip of the rolls and as the hexane evaporates, the phospholipids adhere to the rolls.

A doctor knife scrapes the product from each drum. The solvent vapor is captured and condensed for reuse. The deoiled flakes are conveyed to the subsequent drying step for final hexane removal. This desolventizing step is performed at a temperature such that darkening of the lecithin does not occur. A fluid bed dryer is used and insures solvent residuals of less than 5 ppm. From this dryer, flakes are conveyed to storage bins prior to granulation and/or grinding. The product is generally agglomerated to granules of two mesh sizes. These may be formed with the use of any of the following equipment: tumble agglomerators, extrudeers, disk pellitizers, flow through mixing agglomerators, fluid bed agglomerators and powder agglomerators. Other agglomerators known to those of skill in the art could also be used. A powder agglomeration is used to make two of the sizes of granules. A Shugii flexomix is currently preferred. A powdered form of the product can be easily ground directly from the flakes.

In a further embodiment, the present invention relates to deoiled phosphatide made by any of the above-described methods.

In another embodiment, the present invention relates to a food-grade or pharmaceutical grade lecithin made by any of the above-described methods. The food-grade lecithin may either be used either for animal feed or for human consumption.

In a further embodiment, the present invention relates to food grade or pharmaceutical grade lecithin that has no residual acetone, is virtually oil-free and is characterized by >90 acetone insoluble matter (A.I.) (more preferably, >97 A.I., >99 A.I. or >99.9 A.I.).

None of the information provided above or in the examples below should be construed in any way to limit the scope of the claims.

EXAMPLE 1

To obtain a deoiled lecithin preparation, crude lecithin was mixed with commercial hexane. The triglycerides were separated from the phosphatides through a PVDF membrane (e.g. from Advanced Membrane Technologies, Cal.) having a molecular weight cutoff of 10,000–50,000 daltons. The retentate consisted of virtually oil free (>90 A.T.) phosphatides and was 35–40% phospholipid in 60–65% hexanes.

The preparation was decolorized with bleaching earth. The degree of decolorization will depend upon the wants and needs of those of skill in the art. The bleaching earth was added to a vessel containing a 35–40% deoiled concentrate in hexane. A typical rate of addition was 5–8% earth on a phospholipid mass basis. Tocopherols and/or antioxidants can be added at this point. Preferably mixed tocopherols are added.

Of importance to the process is desolventizing. Desolventizing drums were chrome-plated cast iron or stainless steel. Low pressure steam was added as the heat source. The refined deoiled concentrate was added to the nip of the rolls and as the hexane evaporates, the phospholipids adhered to the rolls.

The desolventizing step was performed at a temperature such that darkening of the lecithin did not occur. A fluid bed dryer was used and insured solvent residuals of less than 5 ppm. From this dryer, flakes were conveyed to storage bins prior to granulation and grinding. Granulation was performed in a Shugii agglomerator.

The finished particles had a U.S. Sieve Size (G cut) of −10 to +20; F cut of −20 to +40, while a finished powder product had a U.S. Sieve Size of −40.

The invention concerns a method of making deoiled phosphatides, particularly lecithin and to the phosphatide or lecithin that is obtained by the process.

All references mentioned herein are incorporated by reference into the disclosure.

Having now fully described the invention by way of illustration and example for purposes of clarity and understanding, it will be apparent to those of ordinary skill in the art that certain changes and modifications may be made in the disclosed embodiments and such modifications are intended to be within the scope of the present invention.

What is claimed is:

1. A method for producing deoiled phosphatides, said method not using acetone as a solvent and comprising:
   a) mixing a crude phosphatide preparation with an alkane;
   b) separating triglycerides from phosphatides through a membrane;
   c) obtaining a retentate containing phospholipids following separation;
   d) decolorizing said retentate with bleaching earth; and
   e) evaporating the alkane from said retentate.

2. The method of claim 1 further comprising the step of granulating in a powder agglomerator.

3. A method for producing deoiled phosphatides, said method not using acetone as a solvent and comprising:
   a) mixing a crude phosphatide preparation with an alkane;
   b) separating triglycerides from phosphatides through a membrane;
   c) obtaining a retentate containing phospholipids following separation;
   d) evaporating alkane from said retentate; and
   e) granulating in a powder agglomeration.

4. A method for producing food grade or pharmaceutical grade deoiled lecithin, said method not using acetone as a solvent and comprising:
   a) mixing crude lecithin with an alkane;
   b) separating triglycerides from phosphatides through a membrane;
   c) obtaining a retentate containing phospholipids following separation;
   d) decolorizing said retentate with bleaching earth; and
   e) evaporating alkane from said retentate.

5. The method of claim 4 further comprising the step of granulating in a powder agglomerator.

6. A method for producing a food grade or pharmaceutical grade of deoiled lecithin, said method not using acetone as a solvent and comprising:
   a) mixing crude lecithin with an alkane;
   b) separating triglycerides from phosphatides through a membrane;
   c) obtaining a retentate containing phospholipids following separation;
   d) evaporating alkane from said retentate; and
   e) granulating in a powder agglomeration.

7. The method of any one of claims 1–6, wherein said phosphatide or lecithin obtained by the method is virtually oil free and is >90 acetone insoluble matter (A.I.).

8. The method of claim 7, wherein said phosphatide or lecithin obtained is >97 A.I.

9. The method of any one of claims 1–6, wherein there is a residual solvent concentration of less than 5 ppm.

10. The method of any one of claims 1–6, wherein said alkane is selected from the group consisting of alkanes with 3–8 carbons, hexane, heptane, pentane, propane, isooctane, butane and cyclohexane.

11. The method of any one of claims 1–3 wherein said crude phosphatide is from a vegetable selected from the group consisting of soybean, corn, cotton-seed, linseed, peanut, canola, rapeseed, safflower and sunflower.

12. The method of any one of claims 4–6 wherein said crude lecithin is from a vegetable selected from the group consisting of soybean, corn, cotton-seed linseed, peanut, canola, rapeseed, safflower and sunflower.

13. The method of any one of claims 1–6 wherein mixed tocopherols are added before evaporating the alkane from the retentate.

14. The method of any one of claims 1–6, wherein said membrane is a polyvinylidine fluoride (PVDF) membrane.

15. The method of claim 14, wherein said membrane has a molecular weight cutoff of 50,000 or less.

16. The method of any one of claims 1–6, wherein step "a", is replaced with supercritical $CO_2$ or $CO_2$ with solvents to separate phosphatides from oil.

17. The method of any one of claims 1–6, wherein tocopherols are added before evaporating the alkanes.

18. The method of any one of claims 1–6, wherein a chrome-plated or stainless steel desolventizing drum is used to remove the alkane.

19. The method of any one of claims 1–6, wherein the phosphatide or lecithin is a modified lecithin.

20. The method of claim 19 wherein the modified lecithin is selected from the group comprising acetylated lecithin, hydroxylated lecithin, hydrogenated lecithin, hydrolysis products of lecithin, chlorinated lecithin, brominated lecithin phosphorylated lecithin, halogenated lecithin, sulfonated lecithin, iodinated lecithin, interesterfied lecithin and enzyme modified lecithin.

21. The method of any one of claims 1, 2, 4 or 5 wherein the decolorizing step is replaced by bleaching with a decolorizer selected from the group consisting of carbon, activated carbon, resins and peroxides.

22. The method of any one of claims 1–6, wherein the phosphatide or lecithin is in the form of crude oil miscella extracted from oil seeds and oil bearing plant materials.

23. The method of any one of claims 1–6, wherein the phosphatide or lecithin is derived from an animal source.

24. The method of any one of claims 1–6, wherein the phosphatide or the lecithin is a fractioned lecithin.

25. The method of claim 24 wherein the fractionated lecithin is selected from the group consisting of phosphatidyl choline, phosphatidyl ethanolamine, phosphatidyl serine, phosphatidyl inositol, phosphatidyl glycerol, diphosphatidyl glycerol, N-acylphosphatidyl ethanolamine, phosphatidic acid and plasmalogen.

26. A deoiled phosphatide made by the method of any one of claims 1–3, wherein the deoiled phosphatide is not a fractionated lecithin.

27. A food grade or pharmaceutical grade lecithin made by the method of any one of claims 4–6, wherein the lecithin is not a fractionated lecithin.

28. The method of claim 3 wherein said alkane is evaporated from the retentate using a desolventizer selected from the group consisting of spray dryers, fluid bed driers with or without vibration, drum driers, belt driers, tumble driers, any of which can be done either as a batch or continuous preparation.

29. The method of claim 3 wherein the agglomeration is accomplished using an agglomerator selected from the group consisting of tumble agglomerators, extruders, disk pellitizers, flow through mixing agglomerators, fluid bed agglomerators and powder agglomerators.

30. A food grade or pharmaceutical grade lecithin that has no residual acetone, is virtually oil-free and is characterized by >90 acetone insoluble matter (A.I.), wherein the lecithin is not a fractionated lecithin.

31. The food grade or pharmaceutical grade lecithin of claim 30 wherein it is characterized by >97 A.I.

32. The food-grade or pharmaceutical grade lecithin of claim 30 wherein the lecithin is an animal lecithin.

* * * * *